United States Patent [19]

Svahn et al.

[11] Patent Number: 4,483,867
[45] Date of Patent: Nov. 20, 1984

[54] ANTIFIBRINOLYTICALLY ACTIVE DERIVATIVES OF TRANEXAMIC ACID

[75] Inventors: Carl M. E. Svahn, Sollentune; Ferenc Merényi, Täby; Lennart E. Karlsson, Vällingby; Gunnar Hanshoff, Järfälla, all of Sweden

[73] Assignee: KabiVitrum AB, Stockholm, Sweden

[21] Appl. No.: 440,699

[22] Filed: Nov. 10, 1982

[30] Foreign Application Priority Data

Nov. 17, 1981 [SE] Sweden ................................. 8106818

[51] Int. Cl.³ ................ A61K 31/365; A61K 31/265; A61K 31/215; A61K 31/24; A61K 31/22; C07C 101/04; C07D 307/77
[52] U.S. Cl. ................................. 424/279; 260/463; 424/301; 424/305; 424/309; 424/311; 549/310; 560/37; 560/125
[58] Field of Search .................. 560/125, 37; 549/310; 424/309, 311, 305, 279, 301; 260/463

[56] References Cited

U.S. PATENT DOCUMENTS 3,939,200  2/1976  Emmons et al. ..................... 560/125
3,995,055  11/1976 Sentoku et al. ...................... 424/309

FOREIGN PATENT DOCUMENTS 0365506  3/1974  Sweden .
0949512  2/1963  United Kingdom .
1580783  2/1980  United Kingdom .

OTHER PUBLICATIONS

Analytical Chemistry, vol. 19, No. 3, pp. 369–373 (1977); Vessman et al.
Derwent Abstract 06434v.
Derwent Abstract 27462f.
Derwent Abstract 46818a.
Derwent Abstract 56916y.
Derwent Abstract 67786r.
Journal of Medicinal Chemistry, vol. 15, No. 3, pp. 247–255 (1972); Okano et al.

Primary Examiner—Natalie Trousof
Assistant Examiner—Patricia M. Scott
Attorney, Agent, or Firm—Pollock, Vande Sande & Priddy

[57] ABSTRACT

Novel antifibrinolytically active compounds of the formula

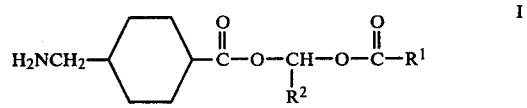

and therapeutically acceptable salt thereof,
wherein
$R^1$ is selected from the group consisting of
(a) alkyl groups containing 1–4 carbon atoms,
(b) alkoxy groups containing 1–4 carbon atoms, (c)

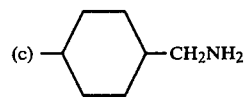

(d)

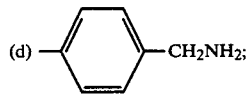

$R^2$ is selected from the group consisting of
(a) H,
(b) alkyl groups containing 1–4 carbon atoms,
(c) —COOR³, wherein $R^3$ is an alkyl group containing 1–4 carbon atoms,
(d) —CONR⁴R⁵, wherein $R^4$ and $R^5$ are the same or different alkyl groups containing 1–3 carbon atoms;
or wherein $R^1$ and $R^2$ represent together the radical

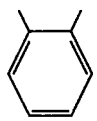

27 Claims, No Drawings

ANTIFIBRINOLYTICALLY ACTIVE DERIVATIVES OF TRANEXAMIC ACID

FIELD OF THE INVENTION

The present invention relates to novel derivatives of tranexamic acid intended for use in medicine and therapeutically acceptable salts thereof; methods for their preparation; pharmaceutical compositions containing the compounds as active ingredient; and the use in medicine of the compounds, particularly for the treatment of ailments which are due to increased fibrinolysis, and for the treatment of hereditary angio-neurotic edema.

BACKGROUND OF THE INVENTION

Tranexamic acid, or trans-4-aminomethylcyclohexanecarboxylic acid:

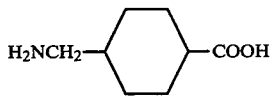
(i)

is used clinically as an antifibrinolytic drug. The trans-isomer is biologically active, while the cis-isomer is practically inactive. The normal route of administration of tranexamic acid is by oral administration, but it can also be administered parenterally, by infusion or by injection. However, because of the limited absorption of tranexamic acid when administered by the oral route—normally 35–40% of administered tranexamic acid is absorbed—fairly high dosages must be prescribed, typically from about 3 to about 6 grams per 24 hours. Such a large intake causes in some patients undesired side effects in the gastro-intestinal tract, probably due to local irritation caused by not absorbed drug.

There is a need for orally active antifibrinolytic drugs with improved absorption properties after oral administration and with reduced undesired gastrointestinal effects. The present inventions provides novel esters of tranexamic acid which possess such properties.

PRIOR ART

Tranexamic acid is disclosed for example in British Pat. No. 949,512. Esters of tranexamic acid are disclosed for example in Journal of Medicinal Chemistry 1972 volume 15 no. 3 pp. 247–255, and in the Derwent abstracts 27462 F, 31374 F, 67786 R, 06434 V, 80109 X, 56916 Y and 46818 A.

DETAILED DESCRIPTION OF THE INVENTION

It has been found according to the present invention that the compounds of the formula

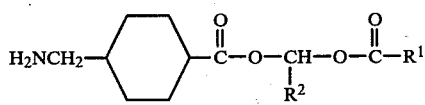
I and therapeutically acceptable salts thereof, wherein
R$^1$ is selected from the group consisting of
  (a) alkyl groups containing 1–4 carbon atoms,
  (b) alkoxy groups containing 1–4 carbon atoms,

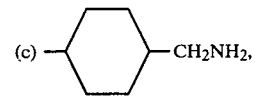

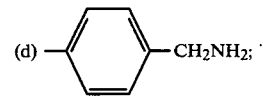

R$^2$ is selected from the group consisting of
  (a) H,
  (b) alkyl groups containing 1–4 carbon atoms,
  (c) —COOR$^3$, wherein R$^3$ is an alkyl group containing 1–4 carbon atoms,
  (d) —CONR$^4$R$^5$, wherein R$^4$ and R$^5$ are the same or different alkyl groups containing 1–3 carbon atoms;
or wherein R$^1$ and R$^2$ represent together the radical

are antifibrinolytically active compounds which after oral administration are absorbed to a considerably higher degree than tranexamic acid as such. The compounds of the formula I are rapidly hydrolyzed in the organism whereby tranexamic acid is liberated and exerts its biological activity.

Illustrative examples of the radicals R$^1$, R$^2$, R$^3$ and R$^4$ are:

R$^1$: CH$_3$, C$_2$H$_5$, CH$_2$CH$_2$CH$_3$, CH(CH$_3$)$_2$, n-butyl, iso-butyl, sec. butyl, tert. butyl, OCH$_3$, OC$_2$H$_5$, OCH$_2$CH$_2$CH$_3$, OCH(CH$_3$)$_2$, n-butoxy, iso-butoxy, sec. butoxy,

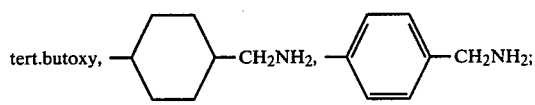

R$^2$: H, CH$_3$, C$_2$H$_5$, CH$_2$CH$_2$CH$_3$, CH(CH$_3$)$_2$, n-butyl, iso-butyl, sec. butyl, tert. butyl, COOCH$_3$, COOC$_2$H$_5$, COO-n-C$_3$H$_7$, COO-n-C$_4$H$_9$, CON(CH$_3$)$_2$,

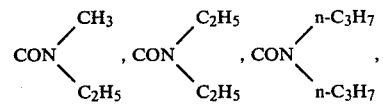

R$_3$: CH$_3$, C$_2$H$_5$, CH$_2$CH$_2$CH$_3$, CH(CH$_3$)$_2$, n-butyl, iso-butyl, sec. butyl, tert. butyl.

R$^4$ and R$^5$: CH$_3$, C$_2$H$_5$, CH$_2$CH$_2$CH$_3$, CH(CH$_3$)$_2$.

Illustrative examples of compounds included in the formula I are given in the following table, where combinations of R$^1$ and R$^2$ are given:

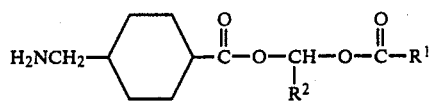

| R¹ | R² |
|---|---|
| CH₃ | H |
| C₂H₅ | H |
| CH₂CH₂CH₃ | H |
| CH(CH₃)₂ | H |
| n-butyl | H |
| isobutyl | H |
| sec.butyl | H |
| tert.butyl | H |
| CH₃ | CH₃ |
| C₂H₅ | CH₃ |
| CH₂CH₂CH₃ | CH₃ |
| CH(CH₃)₂ | CH₃ |
| n-butyl | CH₃ |
| isobutyl | CH₃ |
| sec.butyl | CH₃ |
| tert.butyl | CH₃ |
| CH₃ | C₂H₅ |
| C₂H₅ | C₂H₅ |
| CH(CH₃)₂ | C₂H₅ |
| tert.butyl | C₂H₅ |
| 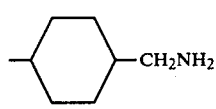 | H |
| 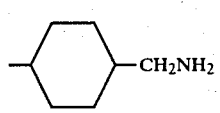 | CH₃ |
| 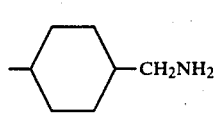 | C₂H₅ |
| 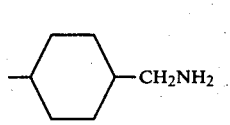 | CON(CH₃)₂ |
| 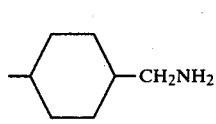 | CON(C₂H₅)₂ |
| 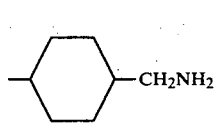 | COOCH₃ |
| 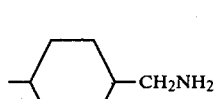 | COOC₂H₅ |
| 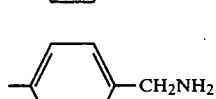 | H |
| 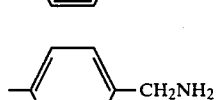 | CH₃ |

-continued

| R¹ | R² |
|---|---|
| 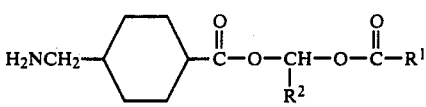 | CON(CH₃)₂ |
| 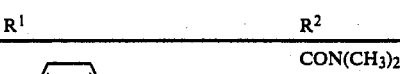 | COOCH₃ |
| 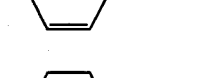 | COOC₂H₅ |
| OCH₃ | H |
| OC₂H₅ | H |
| OCH₂CH₂CH₃ | H |
| OCH(CH₃)₂ | H |
| O—n-butyl | H |
| O—isobutyl | H |
| O—sec.butyl | H |
| O—tert.butyl | H |
| OCH₃ | CH₃ |
| OC₂H₅ | CH₃ |
| OCH₂CH₂CH₃ | CH₃ |
| OC(CH₃)₂ | CH₃ |
| O—n-C₄H₉ | CH₃ |
| O—isobutyl | CH₃ |
| O—sec.butyl | CH₃ |
| O—tert.butyl | CH₃ |
| OCH₃ | C₂H₅ |
| OC₂H₅ | C₂H₅ |

Preferred meanings of the radicals R¹ and R² are:

R¹:
(1) alkyl groups containing 1–4 carbon atoms,
(2) alkoxy groups containing 1–4 carbon atoms,
(3) the radical

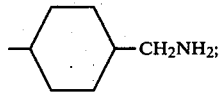

R²:
(1) H
(2) CH₃.

Preferred combinations of the radicals R¹ and R² are:

| R¹ | R² |
|---|---|
| alkyl group containing 1–4 carbon atoms | H |
| alkyl group containing 1–4 carbon atoms | CH₃ |
| alkoxy group containing 1–4 carbon atoms | H |
| alkoxy group containing 1–4 carbon atoms | CH₃ |
| 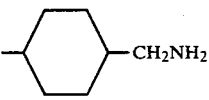 | H |

| $R^1$ | $R^2$ |
|---|---|
| —⟨hexyl⟩—CH$_2$NH$_2$ | CH$_3$ |

Among the preferred compound of the invention are:

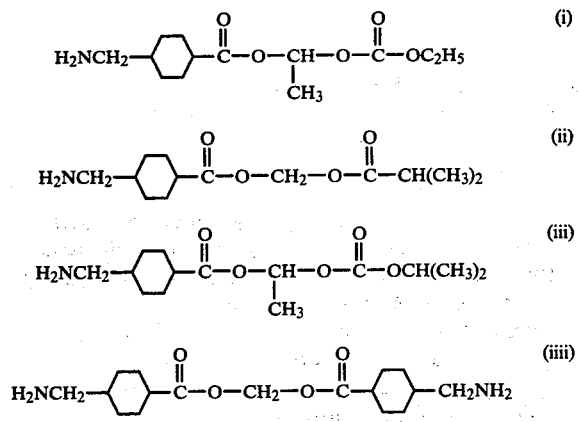

The compound (i) is the preferred compound of the invention. An overriding aspect of the compounds of the invention is that the trans-form of the compounds is preferred.

The compounds of the formula I will occur in cis- and trans-configuration. Compounds of both these configurations, as well as mixtures thereof, are included among the compounds of the present invention. The compounds of trans-configuration are preferred. The cis- and trans-isomers can be separated by known methods.

The area of use of the compounds of the present invention is the same as for tranexamic acid. This means that the compounds will be used as antifibrinolytic agents, that is for combatting ailments in mammals and man which are due to increased fibrinolysis. Increased fibrinolysis may occur for instance during menstruation and also as a result of surgical operations.

Still another area of use for the compounds of the invention is in the treatment of peptic ulcers. At such treatment the compounds may be administered in an amount of from 100 to 2000 mg per day.

Still another area of use for the compounds of the present invention is in the treatment of hereditary angio-neurotic edema.

In clinical practice the compounds of the invention will normally be administered orally, by injection or topically in the form of a pharmaceutical preparation comprising the active ingredient in the form of the original compound or optionally in the form of pharmaceutically acceptable salt thereof, in association with a pharmaceutically acceptable carrier which may be a solid, semisolid or liquid diluent or an ingestible capsule, and such preparations comprise a further aspect of the invention. The compounds may also be used without carrier material. As examples of pharmaceutical preparations may be mentioned tablets, drops, gels, ointments, creams, eyedrops, nasal spray, etc. Usually the active substance will comprise between 0.05 and 99%, or between 0.1 and 99% by weight of the preparation, for example between 0.5 and 20% for preparations intended for injection and between 10 and 90% for preparations intended for oral administration.

The new compounds according to the invention may be administered in the form of salts with physiologically acceptable acids. Suitable acids which may be used are, for example hydrochloric, hydrobromic, sulphuric, fumaric, citric, tartaric, maleic or succinic acid.

The invention further provides pharmaceutical compositions comprising as active ingredient at least one of the compounds according to the invention in association with a pharmaceutical carrier. Such compositions may be designed for example for oral, topical, rectal or parenteral administration.

To produce pharmaceutical preparations in the form of dosage units for oral application containing a compound of the invention in the form of the free base, or a pharmaceutically acceptable salt thereof, the active ingredient may be mixed with a solid, pulverized carrier, for example, lactose, saccharose, sorbitol, mannitol, a starch such as potato starch, corn starch, maize starch or amylopectin, a cellulose derivative or gelatin, and also may include lubricants such as magnesium or calcium stearate or a Carbowax or other polyethylene glycol waxes and compressed to form tablets or centers for dragees. If dragees are required, the centers may be coated, for example, with concentrated sugar solutions which may contain gum arabic, talc and/or titanium dioxide, or alternatively with a lacquer dissolved in easily volatile organic solvents or mixtures of organic solvents. Dyestuffs can be added to these coatings. For the preparation of soft gelatin capsules (pearl-shaped closed capsules) consisting of gelatin and, for example, glycerol, or similar closed capsules, the active substance may be admixed with a Carbowax. Hard gelatin capsules may contain granulates of the active substance with solid, pulverized carriers such as lactose, saccharose, sorbitol, mannitol, starches (for example potato starch, corn starch, or amylopectin), cellulose derivatives or gelatin, and may also include magnesium stearate or stearic acid. Dosage units for rectal application may be in the form of suppositories comprising the active substance in admixture with a Carbowax or other polyethylene glycol waxes. Each dosage unit preferably contains 50 to 500 mg active ingredient.

Liquid preparations for oral application may be in the form of syrups, suspensions or emulsions, for example containing from about 0.1% to 20% by weight of active substance and also, if desired, such adjuvants as stabilizing agents, suspending agents, dispersing agents, flavouring agents and/or sweetening agents.

Liquid preparations for rectal administration may be in the form of aqueous solutions containing from about 0.1% to 2% by weight of active substance and also, if desired, stabilizing agents and/or buffer substances.

For parenteral application by injection the carrier may be a sterile, parenterally acceptable liquid, e.g. pyrogen-free water or an aqueous solution of polyvinyl-pyrrolidone, or a parenterally acceptable oil, e.g., arachis oil and optionally stabilizing agents and/or buffer substances. Dosage units of the solution may advantageously be enclosed in ampoules, each dosage unit preferably containing from 0.1 to 10 mg of active ingredient.

The dosage at which the active ingredients are administered may vary within a wide range and will depend on various factors such as for example the individual requirements of each patient. A suitable oral dosage range may be from 0.5 to 5 g per day.

The pharmaceutical compositions containing the active ingredients may suitably be formulated so that they provide doses within these ranges either as single dosage units or as multiple dosage units.

The compounds of the invention can be prepared by known methods such as

A. reacting a compound of the formula

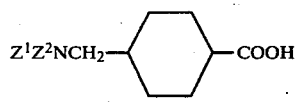   II wherein $Z^1$ and $Z^2$ are H or a protecting group, or a functionally equivalent derivative thereof with a compound of the formula

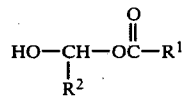   III or a functionally equivalent derivative thereof, wherein $R^1$ and $R^2$ are as defined previously, whereby the possible amine substituent in $R^1$ also may be protected by protecting groups $Z^1$ and $Z^2$, to the formation of a compound of the formula

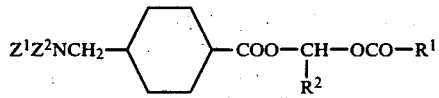   IV whereafter if necessary protecting groups $Z^1$ and $Z^2$ are removed to the formation of a compound of the formula I.

Functionally equivalent derivatives of the hydroxy group in the compound III are for example halogen such as Cl or Br, or I, and sulphonates such as $OSO_2CH_3$,

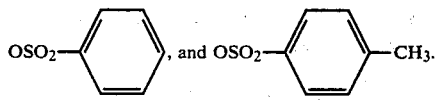

Functionally equivalent derivatives of the carboxyl group in the compound II are for example a carboxylic acid salt such as a metal salt, an ammonium salt or a salt with a substituted ammonium group, for example sodium, potassium, $(C_2H_5)_3N$, $(C_4H_9)_4N^+$, and pyridine salt, or an activated carboxyl group, for example an acid chloride, an alkyl ester, an acid anhydride or a mixed anhydride with formic esters or carboxylic acids, sulphonic or inorganic esters, or derivatives obtained by a reaction between a carboxylic acid and a carbodiimide or similarly functioning compounds such as $N_1N^1$-carbonyldiimidazole or N-ethyl-5-phenylisoxazolium-3'-sulphonate, the derivative of the carboxyl group being a carboxylic acid salt as defined above when the radical OH in the compound III has been replaced with halogen.

The protecting groups $Z^1$ and $Z^2$ are removed in known manner.

The protecting groups $Z^1$ and $Z^2$ are preferably a group which can be removed under neutral or acidic conditions or by hydrogenation, especially catalytic hydrogenation. Examples of such groups are tert. butoxycarbonyl, benzyloxycarbonyl, dibenzyl, triphenylmethyl, alkylcarbonyl and arylcarbonyl.

B. reacting a compound of the formula

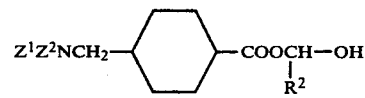   V wherein $Z^1$ and $Z^2$ are H or a protecting group, or a functionally equivalent derivative thereof, with a compound of the formula

   VI wherein $R^1$ is defined above, or a functionally equivalent derivative thereof, whereby the possible amine substituent in $R^1$ also may be protected by protecting groups $Z^1$ and $Z^2$, to the formation of a compound of the formula IV whereafter, if necessary, protecting groups $Z^1$ and $Z^2$ are removed to the formation of a compound of the formula I.

Examples of functionally equivalent derivatives of the compounds V and VI are the same derivatives which are described with regard to compounds II and III in method A.

C. reduction of a compound of the formula

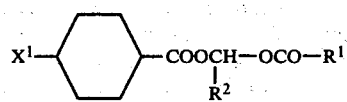   VII wherein $R^1$ and $R^2$ are as defined above and $X^1$ is $-CN$, $-CH_2NO_2$, $-CH_2N_3$, $-CONH_2$ or $-CH=N-OH$ to the formation of a compound of the formula I.

The reduction is carried out in known manner, for example by catalytical hydrogenation.

D. reduction of a compound of the formula

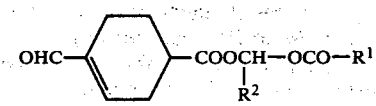   VIII wherein $R^1$ and $R^2$ are as defined above, in the presence of $NH_3$ to the formation of a compound of the formula I.

The reduction may be carried out in known manner for example by catalytical hydrogenation. The $NH_3$ may be present in the form of $NH_4OH$.

E. for the preparation of compounds of the formula I wherein $R^1$ is

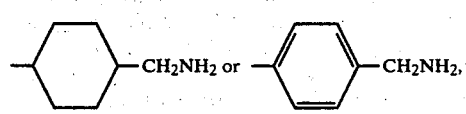

reduction of a compound of the formula

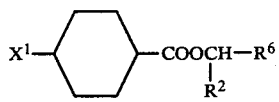

wherein $R^2$ is as defined above, $R^6$ is

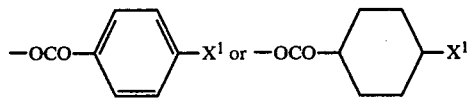

and $X^1$ is —CN, —CH$_2$NO$_2$, CH$_2$N$_3$, —CONH$_2$ or CH=N—OH, to the formation of a compound of the formula I wherein $R^1$ is

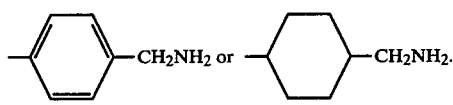

The reduction is carried out in known manner.

F. for the preparation of compounds of the formula I wherein $R^1$ is

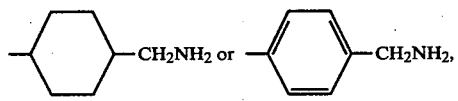

reduction of a compound of the formula

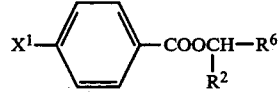

wherein $R^2$, $R^6$ and $X^1$ are as defined above, to the formation of a compound of the formula I wherein $R^1$ is

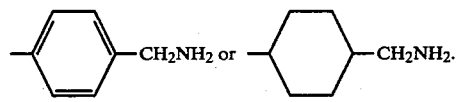

The reduction is carried out in known manner.

G. for the preparation of compounds of the formula I wherein $R^1$ is

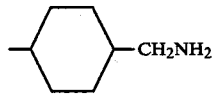

reacting a compound of the formula

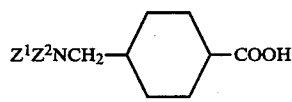

XI wherein $Z^1$ and $Z^2$ are H or a protecting group as defined above, or a functionally equivalent derivative thereof, with a compound of the formula

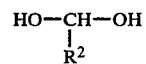

XII wherein $R^2$ is as defined above, or a functionally equivalent derivative thereof, to give a compound of the formula

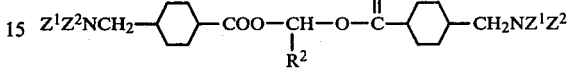

XIII whereafter if necessary protecting groups $Z^1$ and $Z^2$ are removed.

Examples of groups which are functionally equivalent with the carboxyl and hydroxy groups in the formula XI and XII are for example the groups mentioned in Method A above.

H. for the preparation of compounds of the formula I wherein $R^1$ is

reacting a compound of the formula

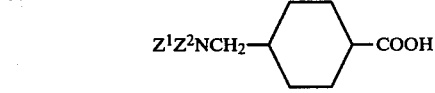

XI and a compound of the formula

XIV in which formulas $Z^1$ and $Z^2$ are H or a protecting group as defined above, or a functionally equivalent derivative thereof with a compound of the formula

HO—CH—OH
    |
    $R^2$

XII wherein $R^2$ is as defined above, or a functionally equivalent derivative thereof, to give a compound of the formula

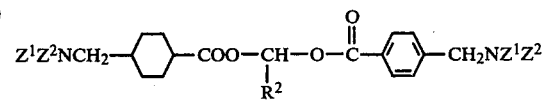

XV whereafter if necessary protecting groups $Z^1$ and $Z^2$ are removed.

Examples of groups which are functionally equivalent with the carboxyl and hydroxy groups in the formula XI, XIV and XII are for example the groups mentioned in Method A above.

In Method H, the protecting groups Z in compound XI and compound XIV are suitably different.

I. For the preparation of a compound of the formula I wherein $R^2$ is $COOR^3$, reacting a compound of the formula

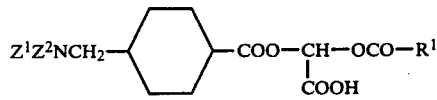   XVI wherein $Z^1$ and $Z^2$ are H or a protecting group as defined in Method A and $R^1$ is as defined above, whereby the possible amine substitutent in $R^1$ also may be protected by protecting groups $Z^1$ and $Z^2$, or a functionally equivalent derivative thereof, with a compound of the formula

HO—$R^3$   XVII wherein $R^3$ is as defined above, or a functionally equivalent derivative thereof, whereafter, if necessary, protecting groups $Z^1$ and $Z^2$ are removed, to the formation of a compound of the formula I wherein $R^2$ is $COOR^3$.

Examples of groups which are functionally equivalent with the carboxyl and hydroxy groups in the formula XVI and XVII are for example the groups mentioned in Method A above.

J. for the preparation of a compound of the formula I wherein $R^2$ is $CONR^4R^5$, reacting a compound of the formula

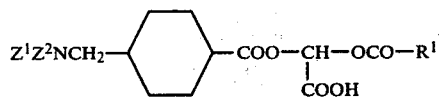   XVIII wherein $R^1$ is as defined above, or a functionally equivalent derivative thereof, with a compound of the formula

   XIX wherein $R^4$ and $R^5$ are as defined above, or a functionally equivalent derivative thereof, whereafter, if necessary, protecting groups $Z^1$ and $Z^2$ are removed, to the formation of a compound of the formula I wherein $R^2$ is $CONR^4R^5$.

Functionally equivalent derivatives of the carboxyl group in compound XVIII are for example an activated carboxyl group such as an acid halide, an alkyl ester, an acid anhydride, a mixed anhydride with formic ester or carboxylic esters, sulphonic or inorganic acids, or derivatives obtained by a reaction between a carboxylic acid and a carbodiimide or similarly functioning compounds such as $N_1N^1$-carbonyldiimidazole or N-ethyl-5-phenyl-isoxazolium-3'-sulphonate.

K. for the preparation of compounds wherein $R^1$ is

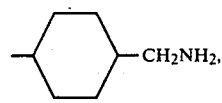

reacting a compound of the formula $R^2$—CHO   XX wherein $R^2$ is as defined above, with a compound of the formula

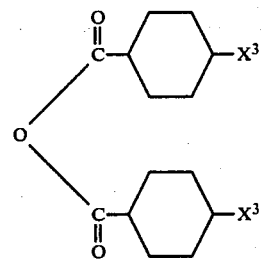   XXI wherein $X^3$ is (a) $CH_2NZ^1Z^2$ wherein $Z^1$ and $Z^2$ are protecting groups as defined in method A, or (b) CN, $CH_2NO_2$, $CH_2N_3$, $CONH_2$ or CH=N—OH, to the formation of a compound of the formula

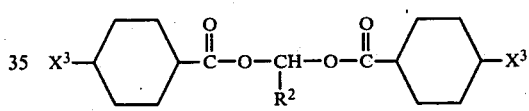   XXII whereafter each of the groups $X^3$ are converted to $CH_2NH_2$ by removal of the protecting groups $Z^1$ and $Z^2$ or by reduction of the groups CN, $CH_2NO_2$, $CH_2N_3$, $CONH_2$, CH=N—OH to the formation of a compound of the formula I wherein $R^1$ is

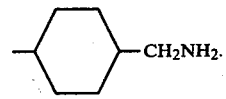

L. for the preparation of compounds of the formula I wherein $R^1$ is an alkyl group containing 1-4 carbon atoms, and $R^2$ is $CH_3$, reacting a compound of the formula

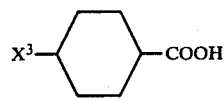   XXIII wherein $X^3$ is as defined in Method K, with a compound of the formula

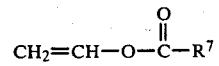   XXIV wherein $R^7$ is an alkyl group containing 1-4 carbon atoms, to the formation of a compound of the formula

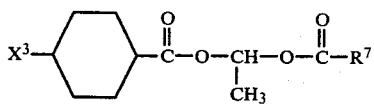 XXV wherein $X^3$ and $R^7$ are as defined above, whereafter $X^3$ is converted to $CH_2NH_2$ as described in Method K to the formation of a compound of the formula I wherein $R^1$ is an alkyl group containing 1-4 carbon atoms and wherein $R^2$ is $CH_3$.

M. for the preparation of compounds of the formula I wherein $R^1$ is

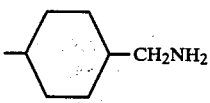

and $R^2$ is $CH_3$, reacting a compound of the formula

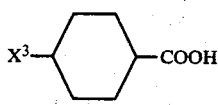 XXIII wherein $X^3$ is as defined in Method K, with a compound of the formula

 XXVI to the formation of a compound of the formula

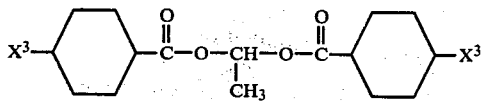 XXVII wherein $X^3$ is as defined above, whereafter $X^3$ is converted to $CH_2NH_2$ as described in Method K to the formation of a compound of the formula I.

If desired, the compound of the formula I obtained by the processes A-M may be converted in known manner to a therapeutically acceptable salt. The compound of the formula I, or a therapeutically acceptable salt thereof, may also if necessary be separated in known manner in its cis- and trans-isomers. As noted above, the main biological activity will reside in the trans-isomer.

The compounds used as starting materials in the processes A-M can be prepared by known methods.

The invention is further illustrated by the following examples.

EXAMPLE 1

Preparation of pivaloyloxymethyl trans-4-aminomethylcyclohexanecarboxylate hydrochloride (Method A)

Chloromethyl pivalate (33.2 g; 0.22 mol) was added to a suspension of sodium bromide (22.4 g; 0,22 mol) in dimethylformamide. After 2 h a solution of trans-4-(tert.-butyloxycarbonylaminomethyl)cyclohexanecarboxylic acid in triethylamine (24 g; 0.24 mol) and dimethylformamide was added. The mixture was stirred overnight at room temperature. The solvent was distilled off and water (1 L) and dichloromethane was added. The organic layer was separated, washed, dried and evaporated to yield 55 g. This product was dissolved in ethyl acetate and cooled. A solution of hydrochloric acid in ethyl acetate was added. After 1 h ether was added. The precipitate was filtered, washed and dried to yield 30.2 g, m.p. 165° C. after crystallisation from acetone.

Calculated for: $C_{14}H_{26}Cl\ NO_4$: C 54.6, H 8.51, N 4.55, O 20.8, Cl 11.5, found: 54.7, 8.38, 4.51, 21.1, 11.7.

EXAMPLE 2

Preparation of phthalidyl trans-4-aminomethylcyclohexanecarboxylate hydrochloride (Method A)

A solution of 3-bromophthalide (70.5 g; 0.33 mol) in dimethylformamide (65 ml) was added dropwise to a cold solution of trans-4-(tert.-butyloxycarbonylaminomethyl) cyclohexanecarboxylic acid (77.1 g; 0.3 mol) in triethylamine (36.4 g; 0.36 mol) and dimethylformamide (195 ml). After 18 h the solvent was evaporated, water (1.5 L) and ethyl acetate (1.5 L) were added. The ethyl acetate extract was washed, dried and evaporated to give 122 g. This was dissolved in ethyl acetate (400 ml) and ethyl acetate/hydrochloric acid was added at ice bath temperature. After 2 h at room temperature, the precipitate was filtered, washed and dried to yield 63.8 g. This substance was dissolved in methanol, filtered through charcoal and precipitated with diethyl ether. Yield 54.4 g (56%), m.p. 212° C.

Calculated for: $C_{26}H_{20}Cl\ NO_4$: C 59.0, H 6.19, N 4.30, O 19.64, Cl 10.88, found: 59.1, 6.18, 4.13, 19.65, 11.15.

EXAMPLE 3

Preparation of 1-(ethyloxycarbonyloxy)ethyl trans-4-aminomethylcyclohexanecarboxylate hydrochloride (Method A)

A solution of trans-4-(tert.-butoxycarbonylaminomethyl) cyclohexanecarboxylic acid (25.7 g; 0.1 mol) and tetrabutylammonium hydrogen sulfate (34 g; 0.1 mol) in 2N sodium hydroxide (100 ml) was extracted with ethanolfree chloroform. The chloroform solution was dried and evaporated to give 50 g. This was dissolved in trichloroethylene (200 ml) and ethyl (1-chloroethyl) carbonate (16.8 g; 0.11 mol) was added. After refluxing for 3 h the solution was washed with dilute sulphuric acid, sodium bicarbonate solution and water. After evaporation of chloroform the residue was dissolved in ethyl acetate cooled to 0° C. To this solution a cold solution of hydrochloric acid in ethyl acetate was added. After 3 h at ice bath temperature the solvent was evaporated to give 23 g. This was dissolved in isopropyl alcohol and precipitated with diisopropyl ether. Yield 15 g (49%), m.p. 139° C.

Calculated for: $C_{13}H_{24}Cl\ NO_5$: C 50.4, H 7.81, N 4.51, O 25.8, Cl 11.5, found: 50.4, 7.82, 4.80, 25.4, 11.7.

EXAMPLE 4

Preparation of 1-(isopropyloxycarbonyloxy)ethyl trans-4-aminomethylcyclohexanecarboxylate hydrochloride (Method A)

Isopropyl (1-chloroethyl) carbonate (22 g; 0.3 mol) was added to sodium bromide (13.5 g; 0.13 mol) in dimethylformamide (120 ml). This mixture was stirred for 3 h and then added to trans-4(-tert.-butoxycarbonylaminomethyl)cyclohexane carboxylic acid (30.8 g; 0.12 mol), dissolved in dimethylformamide (450 ml)

and triethylamine (24 g; 0.24 mol). This mixture was stirred at 120° C. for 60 h. The solvent was distilled off and the residue partitioned between ether and water. The ether layer was washed, dried and evaporated to give 9 g of an oil. This oil was dissolved in ethyl acetate and treated with hydrochloric acid in ethyl acetate. After evaporation of the solvent and recrystallization from acetone 3.3 g of product, m.p. 158° C. was obtained.

Calculated for: $C_{14}H_{26}$ Cl $NO_5$: C 51.9, H 8.09, N 4.33, O 24.7, Cl 11.0, found: 51.8, 8.09, 4.13, 24.2, 11.1.

The isopropyl (1-chloroethyl) carbonate used as starting material was prepared as follows.

1-chloroethyl chloroformate (28.5 g; 0.2 mol) was mixed with isopropyl alcohol (13.2 g; 0.22 mol) and heated to 90° C. After cooling to room temperature the product was washed with water and sodium bicarbonate solution and dried. 30 g was obtained. NMR spectrum ($CDCl_3$) 1.40 ($CH_3$)$_2$C; $\delta$1.85 $CH_3$C; $\delta$5.10 C—CH—C; $\delta$6.45 OCH(C)Cl.

EXAMPLE 5

Preparation of 1-(acetyloxy) ethyl trans-4-aminomethylcyclohexanecarboxylate (Method A)

1-(acetyloxy)ethyl chloride (24.5 g; 0.2 mol) was mixed with sodium bromide (21 g; 0.2 mol) in dimethylformamide (400 ml). To this mixture after 2 h of stirring trans-4-(tert.-butoxycarbonylaminomethyl)cyclohexanecarboxylic acid (64.3 g; 0.25 mol) and triethylamine (50 g; 0.5 mol) were added. This mixture was stirred for 24 h at 35° C. Water and diethyl ether was added. The organic phase was washed, dried and evaporated to give 8.5 g. This product was dissolved in ethyl acetate, cooled and mixed with ethylacetate containing hydrochloric acid. Diethyl ether was added after 3 h and the precipitate was filtered off, washed and dried. 5 g was obtained which after recrystallization from an isopropyl alcohol/isopropyl ether mixture yielded 4.5 g, m.p. 126° C.

Calculated for: $C_{12}H_{22}Cl$ $NO_4$: C 51.5, H 7.93, N 5.01, O 22.9, Cl 12.7, found: 51.4, 7.93, 4.41, 23.2, 12.8.

EXAMPLE 6

Preparation of isobutyryloxymethyl trans-4-aminomethylcyclohexanecarboxylate (Method A)

Sodium bromide (3.8 g; 0.037 mol and isobutyryloxymethyl chloride (5.1 g; 0.037 mol) was mixed with dimethylformamide (40 ml) and stirred for 3 h at room temperature. Trans-4-(tert.-butoxycarbonylaminomethyl)cyclohexane carboxylic acid (15.4 g; 0.06 mol) dissolved in dimethylformamide (100 ml) and triethylamine (12 g; 0.12 mol) was added and the stirring continued for 100 h at room temperature. The solvent was evaporated and water and diethylether were added. The ether layer was washed, dried and evaporated to give 6.1 g. This product was dissolved in ethyl acetate and ethyl acetate/hydrochloric acid was added. After 3 h at room temperature ether was added and the precipitate collected. Yield 3.5 g., m.p. 100° C.

The product was dissolved in chloroform. Some undissolved material was filtered off and the solution was evaporated. M.p. 104° C.

Calculated for: $C_{13}H_{24}Cl$ $NO_4$: C 53.2, H 8.23, N 4.77, O 21.8, Cl 12.1, found: 53.5, 7.78, 4.65, 21.2, 12.1.

The isobutyryloxymethyl chloride used as starting material was prepared as follows:

Isobutyryl chloride (53 g; 0.5 mol) was mixed with paraformaldehyde (15 g; 0.5 mol) and treated to 90° C. The reaction was started by adding a catalytical amount of zinc chloride. After 3 h the mixture was extracted with pentane. The pentane solution was washed, dried and evaporated to yield 44 g. This product was distilled at 44°–48° C. at 0.5 kPa.

EXAMPLE 7

Preparation of 1-(isobutyryloxy)ethyl trans-4-aminomethylcyclohexanecarboxylate (Method A)

Sodium bromide (13.5 g; 0.132 mol) and 1-(isobutyryloxy)ethyl chloride (19.9 g; 0.132 mol) were added to dimethylformamide (120 ml). After 3 h at room temperature a solution of trans-4-(tert.-butoxycarbonylaminomethyl) cyclohexanecarboxylic acid (30.8 g; 0.12 mol) and triethylamine (24 g; 0.24 mol) in dimethylformamide (200 ml) was added. The mixture was stirred at room temperature for 60 h and then the solvent was evaporated. Water and diethylether were added and the ether layer was separated, washed, dried and evaporated to yield 13 g of an oil. The oil was dissolved and ethyl acetate and ethyl acetate/hydrochloric acid was added. Diethyl ether was added after 3 h and the precipitate was collected. Yield 2.5 g, m.p. 100° C.

Calculated for: $C_{14}H_{26}Cl$ $NO_4$: C 54.6, H 8.51, H 4.55, O 20.8, Cl 11.5, found: 54.4, 8.53, 4.31, 20.1, 11.7.

EXAMPLE 8

Preparation of 1-(pivaloyloxy)ethyl trans-4-aminomethylcyclohexanecarboxylate hydrochloride (Method C)

A solution of (1-pivaloyloxy)ethyl trans-4-cyanocyclohexanecarboxylate (4.4 g; 1.5 mmol) in ethyl alcohol and chloroform was hydrogenated, using platinumoxide (0.5 g) as a catalyst. After 20 h at room temperature catalyst was filtered off and the solvent evaporated. The product was recrystallized from a mixture of isopropyl alcohol and diisopropyl ether. Yield 1.7 g, m.p. 85° C.

Calculated for: $C_{15}H_{28}Cl$ $NO_4$: C 56.0, H 8.77, N 4.35, O 19.9, Cl 11.0, found: 56.0, 8.94, 4.45, 19.7, 11.3.

In the same manner as described in Example 8 the following compounds were prepared:

EXAMPLE 9

Preparation of 1-(ethyloxycarbonyloxy)ethyl trans-4-aminomethylcyclohexanecarboxylate hydrochloride The title compound, m.p. 139° C. was obtained from 1-(ethyloxycarbonyloxy)ethyl trans-4-cyanocyclohexanecarboxylate.

EXAMPLE 10

Preparation of isobutyryloxymethyl trans-4-aminomethylcyclohexanecarboxylate

The title compound, m.p. 104° C. was obtained from isobutyryloxymethyl trans-4-cyanocyclohexanecarboxylate, m.p. 33°–35° C.

EXAMPLE 11

Preparation of methandiol
bis-(trans-4-aminomethylcyclohexanecarboxylate)
dihydrochloride (Method E)

To a solution of methandiol bis-(trans-4-cyanocyclohexanecarboxylate) (8.5 g) in 200 ml glacial acetic acid, was added a catalyst (5% palladium on carbon) 1 g, and this mixture was hydrogenated in a Parr-apparatus for 5 h at 0.4 MPa. The catalyst was filtered off and the solvent was evaporated. The residue was dissolved in a mixture of ethyl acetate, isopropyl alcohol and hydrochloric acid dissolved in ethyl acetate was added. The crystalline precipitate was crystallized from isopropyl alcohol. Yield 3.2 g, mp. 270° C.

Calculated for: $C_{17}H_{32}N_2O_4Cl$: C 51.2, H 8.08, N 7.02, O 16.0, Cl 17.8, found: 49.4, 8.09, 7.11, 15.8, 17.9.

The methandiol bis-(trans-4-cyanocyclohexanecarboxylate) used as starting material was prepared as follows:

A solution of trans-4-cyanocyclohexanecarboxylate (7.7 g; 0.05 mol) in tetrabutylammonium hydrogen sulfate in 2N sodium hydroxide was extracted three times with methylene dichloride. The combined organic solution was dried and refluxed for 120 h. The solution was washed with diluted sulphuric acid, water and diluted sodium hydrogen carbonate solution, dried and evaporated. Yield 6.8 g m.p. 94° C. after crystallization from isopropyl alcohol.

Calculated for: $C_{17}H_{22}N_2O_4$: C 64.1, H 6.97, N 8.80, O 20.1, found: 64.2, 6.97, 8.66, 20.5.

EXAMPLE 12

Preparation of 1,1-ethandiol
bis-4-aminomethylcyclohexanecarboxylate)
dihydrochloride (Method F)

A solution of 1,1-ethandiol trans-4-cyanocyclohexanecarboxylate 4-cyanobenzoate (4.4 g; 0.0134 mol) in absolute ethanol and chloroform was hydrogenated for 20 h at 22° C. in a Parr-apparatus at 3.4 MPa with platinium oxide as a catalyst. The catalyst was filtered off and the solvent evaporated to yield 5.0 g. After recrystallization from 2-propanol containing methanol 2.5 g of the title compound was obtained, m.p. 260° C.

Calculated for: $C_{18}H_{34}N_2O_4Cl_2$: C 52.3, H 8.29, N 6.78, O 15.5, Cl 17.2, found: 52.1, 8.22, 6.55, 15.5, 16.9.

The starting material used in Example 12 was prepared as follows.

(a) 1-(trans-4-cyanocyclohexanoyloxy)ethyl chloride trans-4-cyanocyclohexanecarboxylic acid (7.7 g; 0.05 mol) and thionyl chloride (8.0 g; 0.066 mol) was mixed and refluxed for 30 min. Excess thionyl chloride was evaporated in vacuum. Paraldehyde (2.5 g; 0.062 mol) and a catalytic amount of zinc chloride were added and the mixture was heated at 90° C. for 1½ h with stirring. The cooled mixture was extracted with ether, washed with sodium bicarbonate solution, dried and evaporated, the product was distilled at 112° C./1 Pa. Yield 6.5 g of an oil.

(b) 1,1-Ethandiol trans-4-cyanocyclohexylcarboxylate 4-cyano benzoate

A solution of 4-cyanobenzoic acid (11 g; 0.075 mol) and tetrabutylammonium hydrogensulfate (25.5 g; 0.075 mol) dissolved in 2M sodium hydroxide (80 ml) was extracted with ethanolfree chloroform. The solvent was dried and evaporated. The residue was dissolved in 600 ml trichloroethylene and 1-(trans-4-cyanocyclohexanoyloxy)ethyl chloride (10.8 g; 0.05 mol) was added and the solution was refluxed for 8 h. The solution was washed, dried and the solvent was evaporated to yield 15.8 g, m.p. 105° C. after crystallization from ethanol.

Calculated for: $C_{18}H_{18}N_2O_4$: C 66.2, H 5.36, N 8.59, O 19.6, found: 66.2, 5.54, 8.46, 20.0.

EXAMPLE 13

Preparation of 1,1-Ethandiol
bis-(trans-4-aminomethylcyclohexanecarboxylate)
dihydrochloride (Method F)

1,1-Ethandiol bis-(trans-4-cyanocyclohexanecarboxylate) (6 g) was dissolved in a mixture of anhydrous ethanol and chloroform. Platinum oxide (1 g) was added and the mixture was hydrogenated at 3.1 MPa at 22° C. for 15 h. The catalyst was filtered off and the solvent evaporated. The product was crystallized from a mixture of 2-propanol and methanol. Yield 5.5 g, m.p. 260° C.

Calculated for: $C_{18}H_{34}N_2O_4Cl_2$: C 52.3, H 8.29, N 6.78, O 15.5, Cl 17.2, found: 51.6, 8.33, 6.97, 15.6, 17.4.

The starting material used in Example 13 was prepared as follows.

1,1-Ethandiol
bis-(trans-4-cyanocyclohexanecarboxylate)

Trans-4-cyanocyclohexanecarboxylic acid (11.5 g; 0.075 mol) and tetrabutylammonium hydrogen sulfate (25.5 g; 0.075 mol) was dissolved in 2M sodium hydroxide and extracted with ethanolfree chloroform. The chloroform solution was dried and the solvent evaporated. The residue was dissolved in trichloroethylene (600 ml) and 1-(trans-4-cyanocyclohexanoyloxy)ethyl chloride (10.8 g; 0.05 mol) was added. The solution was refluxed for 8 h. It was then washed, dried and evaporated. Yield 17.1 g, m.p. 75°–76° C.

EXAMPLE 14

1,1-Propandiol
bis-(trans-4-aminomethylcyclohexanecarboxylate)
dihydrochloride (Method F)

The title compound, m.p. 270° C., was obtained from 1,1-propandiol bis-(trans-4-cyanocyclohexanecarboxylate) in analogy with Example 13. M.p. 270° C. The NMR spectrum was in accordance with the expected structure.

Calculated for: $C_{19}H_{36}Cl_2N_2O_4$: C 53.4, H 8.49, N 6.56, O 15.3, Cl 16.6, found: 52.5, 8.51, 6.46, 14.8, 16.0.

The starting material used in Example 14, 1,1-propandiol bis-(trans-4-cyanocyclohexanecarboxylate) was an oil which was obtained from 1-(trans-4-cyanocyclohexanoyloxy)propyl chloride as for 1,1-ethandiol bis-(trans-4-cyanocyclohexanecarboxylate).

1-(trans-4-cyanocyclohexanoyloxy)propyl chloride was an oil which was obtained in the same manner as 1-(trans-4-cyanocyclohexanoyloxy)ethyl chloride (Example 12a).

EXAMPLE 15

Preparation of methanediol
bis-(trans-4-aminomethylcyclohexanecarboxylate)
dihydrochloride (Method G)

Diiodomethane (53.6 g; 0.2 mol), trans-4-(tert.-butyloxycarbonylaminomethyl)cyclohexanecarboxylic acid (51.4 g; 0.2 mol) and triethylamine (44 g; 0.44 mol)

was dissolved in dimethylformamide (400 ml) and stirred at 45° C. for 144 h. Additional triethylamine (44 g; 0.44 mol) was added and the stirring was continued at 70° C. for another 96 h. The solvent was evaporated on vacuum. Yield 163 g. 5.4 g of this crude material was dissolved in ethyl acetate (100 ml) and hydrochloric acid in ethyl acetate was added (150 ml). After addition of ether (2.5 L) a precipitate was obtained (3.7 g). This was dissolved in methanol and precipitated with acetone. Yield 2.7 g, m.p. 270° C.

Calculated for: $C_{17}H_{32}N_2Cl_2O_4$: C 51.1, H 8.08, N 7.02, O 16.0, Cl 17.8, found: 51.1, 7.99, 6.89, 15.9, 17.1.

EXAMPLE 16

Preparation of 2,2-dihydroxy-N,N-dimethylacetamide bis-(trans-4-aminomethylcyclohexanecarboxylate) (Method G)

(a) 2,2-Dihydroxy-N,N-dimethylacetamide bis-[trans-4-(tert.-butyloxycarbonylaminomethyl)cyclohexanecarboxylate]

Sodium bromide (10.2 g; 0.1 mol) and 1,1-dichloro-N,N-dimethylacetamide (7.8 g; 0.05 mol) was added to dry dimethylformamide (100 ml) and the mixture was stirred for 4 h. Triethylamine (20.7 g; 0.2 mol) and trans-4-(tert.-butyloxycarbonylaminomethyl)cyclohexanecarboxylic acid (25.7 g; 0.1 mol) dissolved in dimethylformamide was added. The mixture was stirred for 84 h at 50° C. The solvent was evaporated and the residue was taken up into diethylether and washed, dried and evaporated. The oily residue was stirred with pentane. Yield 7 g, m.p. 110° C.

Calculated for: $C_{30}H_{51}N_3O_9$: C 60.3, H 8.60, N 7.03, O 24.0, found 59.8, 8.49, 7.06, 23.8.

(b) 2,2-Dihydroxy-N,N-dimethylacetamide bis-(trans-4-aminomethylcyclohexanecarboxylate)

2,2-Dihydroxy-N,N-dimethylacetamide bis-[trans-4-(tert.-butyloxycarbonylaminomethyl)cyclohexanecarboxylate] (3 g) was dissolved in ethyl acetate (50 ml) and ethyl acetate containing hydrochloric acid (50 ml) was added. After 2 h the solvent was evaporated and the residue dissolved in methanol and ether was added. The precipitate formed (0.9 g) had a m.p. of 220° C.

Calculated for: $C_{20}H_{37}Cl_2N_3O_5$: C 51.1, H 7.93, N 8.93, O 17.0, Cl 15.1, found: 50.0, 7.93, 8.61, 17.0, 15.1.

EXAMPLE 17

2,2-Dihydroxy-N,N-diethylacetamide bis-(trans-4-aminomethylcyclohexane carboxylate) (Method G)

The title compound was obtained from 1,1-dibromo-N,N-diethylacetamide and trans-4-(tert.butyloxycarbonylaminomethyl)cyclohexane carboxylic acid in analogy with Example 16. M.p. 220° C.

Calculated for: $C_{22}H_{41}Cl_2N_3O_5$: C 53.0, H 8.29, N 8.43, O 16.1, Cl 14.2, found: 52.9, 8.36, 8.19, 16.3, 14.2.

EXAMPLE 18

Preparation of ethyl bis-(trans-4-aminomethyl cyclohexanecarbonyloxyacetate (Method G)

The title compound m.p. 150° C. was obtained from ethyl bis-[trans-4-(tert.butyloxycarbonylaminomethyl)-cyclohexanecarbonyloxy] acetate, m.p. 126° C., in the same way as described in Example 16.

Calculated for: $C_{20}H_{36}N_2O_6Cl_2$: C 51.0, H 7.10, N 5.94, O 20.4, Cl 15.0, found: 50.0, 7.65, 6.09, 19.9, 15.1.

EXAMPLE 19

Preparation of bis-(pivaloyloxymethyl trans-4-aminomethylcyclohexanecarboxylate) fumarate To a solution of pivaloyloxymethyl trans-4-aminomethylcyclohexanecarboxylate (1 g; 4 mmol) in ethyl acetate (200 ml) a solution of fumaric acid (0.35 g; 3 mmol) in methanol (10 ml) was added. The solvent were evaporated and the residue was treated with diisopropyl ether. A crystalline product, m.p. 158° C. was obtained.

Calculated for: $C_{32}H_{54}N_2O_{12}$: C 58.3, H 8.26, N 4.25, O 29.1, found: 57.9, 8.18, 4.33, 28.9.

EXAMPLE 20

Preparation of methandiol bis-(4-aminomethylcyclohexanecarboxylate) dihydrochloride (Method F)

Methandiol bis-4-cyanobenzoate (2 g; 0.014 mol) was dissolved in a mixture of absolute ethanol and chloroform and hydrogenated for 5 h at 40° C. and 3.5 MPa in the presence of platinum oxide (0.3 g). The catalyst was filtered off and the solvent evaporated. The residue was taken up in isopropanol and filtered. Diisopropyl ether was added and the precipitete was collected. Yield 1.3 g, m.p. 250° C.

Calculated for: $C_{17}H_{32}N_2O_4Cl$: C 51.2, H 8.08, N 7.02, Cl 17.8, found: 50.3, 7.92, 7.01, 17.8.

The starting material used in Example 20 was prepared as follows:

Methandiol bis-4 cyanobenzoate 4-cyanobenzoic acid (29.4 g; 0.2 mol) was dissolved in 400 ml 1M sodium hydroxide and extracted with dichloromethane. The dichloromethane solution was refluxed for 96 h. The solution was washed with diluted sulphuric acid, water and sodium bicarbonate solution and dried. On evaporation of the solvent 20.1 g, m.p. 208° C., was obtained.

Calculated for: $C_{17}H_{10}N_2O_4$: C 66.7, H 3.29, N 9.15, O 20.9, found: 66.5, 3.31, 8.95, 21.2.

EXAMPLE 21

Preparation of methandiol trans-4-aminomethylcyclohexanecarboxylate 4-aminomethylbenzoate dihydrochloride (Method H)

Tetrabutylammonium trans-4-(benzyloxycarbonylaminomethyl)-cyclohexanecarboxylate (42.5 g; 0.08 mol) and tetrabutylammonium 4-(tert.-butyloxycarbonylaminomethyl)benzoate (39.4 g; 0.08 mol) was refluxed in dichloromethane (800 ml) for 120 h. After washing and drying and evaporation of solvent 31 g of an oil was obtained. This oil was dissolved in glacial acetic acid and hydrochloric acid dissolved in acetic acid was added. After 3 h a precipitate (11.7 g) was collected, m.p. >270° C. This precipitate was discarded.

To the mother liquor 11.7 g diethyl ether was added and a precipitate was collected, 7.0 g. This product was recrystallized from 2-propanol several times to yield 2.3 g of methandiol trans-4-(benzyloxycarbonylaminomethyl)cyclohexanecarboxylate 4-aminomethylbenzoate hydrochloride, m.p. 162° C. 0.7 g of this product was dissolved in 50 ml acetic acid and hydrogenated at atmospheric pressure using 10% palladium on carbon as a catalyst. After 20 h the catalyst was filtered off and hydrochloric acid dissolved in ethyl acetate was added.

The solvent was evaporated. The product was crystallized from isopropyl alcohol-diisopropyl ether mixtures. Yield 0.3 g, m.p. 240° C.

Calculated for: $C_{17}H_{26}N_2O_4Cl_2$: C 51.9, H 6.66, N 7.12, Cl 18.0, found: 50.1, 6.87, 7.19, 17.5.

The following examples illustrate how the compounds of the invention can be incorporated in pharmaceutical compositions:

EXAMPLE 22

Tablets

Each tablet contains:
Active substance, in the form of its

| | |
|---|---|
| hydrochloride | 500.0 mg |
| Cellulose | 100.0 mg |
| Polyvinylpyrrolidon | 20.0 mg |
| Talc | 15.0 mg |
| Magnesium stearate | 15.0 mg |
| | 650.0 mg |

EXAMPLE 23

Suppositories

Each suppository contains:
Active substance, in the form of its
hydrochloride—300.0 mg,
Ascorbyl palmitate—1.0 mg,
Suppository base (Imhausen H)—ad 2.000.0 mg.

EXAMPLE 24

Gel

Active compound in form of its
hydrochloride—50 mg,
Liquid paraffin—190 mg,
White soft paraffin—760 mg.

EXAMPLE 25

Syrup

Active compound in form of its
hydrochloride—100 mg,
Sorbitol—180 mg,
Sorbic acid—1 mg,
Sodiumpyrosulfite—0.1 mg,
Aroma—0.1 mg,
purified water—ad 1 ml.

EXAMPLE 26

Solution

Active compound in form of its
hydrochloride—100 mg,
Distilled water—ad 1 ml.

EXAMPLE 27

Ointment

Active compound in form of its
hydrochloride—50 mg,
Cotton seed oil—28.5 mg,
Cholesterol—28.5 mg,
White soft paraffin—893 mg.

Biological tests

In the biological tests described in sections A, B and C below, the test compounds were used in trans form and in the form of hydrochloride salt. The test results given in Tables 1 and 2 are average values.

A. In vivo test—absorption of compounds of the invention in rats after oral administration Rats were chosen to study the absorption after oral administration of compounds of the invention which are esters of tranexamic acid. Absorption of tranexamic acid itself is very poor in rats.

The determination of absorption in the rats was performed in the following way: Male rats in groups of three or four were given the test compound by gavage (1 mmol/kg-0.1 mmol/kg, 2 ml/kg). The urine was collected at the intervals 0–6, 6–24, 24–48 and 48–72 hours. At the end of each interval the cages were rinsed with 20 ml of distilled water, which also was collected and analysed. The urine sampls were then analysed for their content of tranexamic acid by a gaschromatographic method according to Wessman J., Strömberg S., Anal. Chem. 49 (1977) 369. The results are shown in table 1, where the total absorption is given as the molar amount of tranexamic acid which was recovered in the urine samples compared to the amount of administered test compound, also calculated as tranexamic acid.

TABLE 1

Absorption of compound of the invention after oral administration

Test compound $H_2NCH_2$—⟨cyclohexyl⟩—$COOCH(R^2)$—$OCO$—$R^1$

| $R^1$ | $R^2$ | Absorption Mole % (average values of four tests) |
|---|---|---|
| Tranexamic acid (reference) | | 11 ± 1.4 |
| $CH_3$ | $CH_3$ | 59 ± 6 |
| $CH(CH_3)_2$ | H | 53 ± 3 |
| $CH(CH_3)_2$ | $CH_3$ | 69 ± 3 |
| $C(CH_3)_3$ | H | 60 ± 10 |
| $C(CH_3)_3$ | $CH_3$ | 76 ± 4 |
| $OCH_2CH_3$ | $CH_3$ | 67 ± 11 |
| $OCH(CH_3)_2$ | $CH_3$ | 87 ± 14 |
| (phenyl) ($R^1$ and $R^2$ together) | | 56 ± 11 |
| ⟨cyclohexyl-$CH_2NH_2$⟩ H | | 66 ± 11 |
| ⟨cyclohexyl-$CH_2NH_2$⟩ $COOCH_2CH_3$ | | 63 ± 8 |
| ⟨cyclohexyl-$CH_2NH_2$⟩ $CON(CH_3)_2$ | | 55 ± 18 |
| ⟨phenyl-$CH_2NH_2$⟩ H | | 34 ± 9 |

It is seen in Table 1 that all of the tested compounds were absorbed to a much higher degree than tranexamic acid. In particular, the compound where $R^1$ is $OCH(CH_3)_2$ and $R^2$ is $CH_3$ was absorbed to a very high degree, or 87%. Tranexamic acid was absorbed to 11%.

B. In vitro test—hydrolysis of compounds of the invention in phosphate buffer and in human plasma The compounds of the present invention, which are esters of tranexamic acid, are converted to tranexamic acid in vivo either during the absorption through the gastro-intestinal wall or by enzymes present in the blood. In order to test the stability of compounds of the invention the half life in human plasma of a number of compounds of the invention was compared to the half life of the same ester in a phosphate buffer of the same pH. The half life, that is, the time within which the amount of unhydrolysed test compound is reduced by 50%, was calculated from the decrease of intact test compound with time. This decrease of intact test compound was monitored by UV-detection at 210 nm using high performance liquid chromatography (HPLC) in the reversed phase mode with mixtures of methanol and phosphate buffer as eluents. The stability in plasma was studied by addition of 50–100 ml of a stock solution of the test compound to 500–1000 ml of plasma thermostated to 37° C. The concentration of the test compound in plasma amounted to $2.3 \cdot 10^{-3} M$. The plasma samples were injected directly into the column after filtration. The half life in buffer solution were determined in the same way except that no filtration was needed. The results are given in Table 2.

TABLE 2

Half life of esters of tranexamic acid in phosphate buffer of pH 7.5 and in human plasma Test compound $$H_2NCH_2-\bigcirc-\overset{O}{\underset{\|}{C}}-O-\underset{R^2}{\overset{|}{C}H}-O-\overset{O}{\underset{\|}{C}}-R^1$$

| $R^1$ | $R^2$ | Half life in phosphate buffer pH 7.5 (minutes) | human plasma (minutes) |
|---|---|---|---|
| $CH_3$ | $CH_3$ | $4.08 \cdot 10^3$ | 9 |
| $CH(CH_3)_2$ | H | $2.16 \cdot 10^3$ | 0.5 |
| $C(CH_3)_3$ | H | $8.82 \cdot 10^3$ | 5 |
| $OCH_2CH_3$ | $CH_3$ | $5.40 \cdot 10^3$ | 1.5 |
| 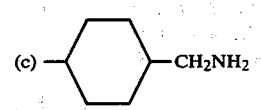 | H | $1.56 \cdot 10^3$ | 1.5 |
| 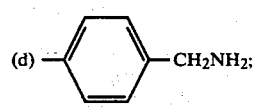 | $CH_3$ | $4.20 \cdot 10^3$ | 11 |

It is seen in Table 2 that the tested compounds of the invention were hydrolyzed very rapidly in human plasma compared to the rate of hydrolysis in phosphate buffer.

C. Antifibrinolytic activity compared to tranexamic acid

The antifibrinolytic properties of tranexamic acid and a number of compounds of the invention were tested in an artificial circulating blood system, the chandler loop (Chandler, A. B., In vitro thrombolytic coagulation of blood. A method for producing a thrombus. Lab.Invest. 7, 110, 1958.) Human blood was mixed with $^{125}$I-labelled fibrinogen, divided into 1.5 ml portions and filled into plastic tubings. After recalcification the loops were rotated for 24 hours during which $^{125}$I-labelled clots were formed. Fibrinolysis as measured with release of $^{125}$I-labelled fibrin degradation products from the clot, was initiated by adding 20 PU/ml of porcine tissue activator to the loops. Clot lysis was followed during six hours and the cumulative release of $^{125}$I FDP was plotted v.s. time of lysis. When tranexamic acid was added to the system before addition of tissue activator, clot lysis was inhibited in a dose dependent manner. The effect on the clot lysis of compounds of the invention was tested in this system and compared to the inhibitory effect of tranexamic acid. The mean inhibitory effect of the test compounds at a concentration of 1 micromole/liter is listed in Table 3. No significant difference ($p > 0.05$) between the antifibrinolytic effect of tranexamic acid and the tested compounds of the invention was found in this test system.

TABLE 3

Antifibrinolytic effect of compounds of the invention compared to the antifibrinolytic effect of tranexamic acid.

Test compound $$H_2NCH_2-\bigcirc-COOCH-OCO-R^1\atop\phantom{H_2NCH_2-\bigcirc-COO}\overset{|}{R^2}$$

| $R^1$ | $R^2$ | Percent inhibition of fibrinolytic activity induced by porcine tissue activator |
|---|---|---|
| Tranexamic acid (reference) | | $25.6 \pm 3.9$ |
| $CH_3$ | $CH_3$ | $19.5 \pm 4.7$ |
| $CH(CH_3)_2$ | H | $32.4 \pm 5.3$ |
| $CH(CH_3)_2$ | $CH_3$ | $23.8 \pm 5.7$ |
| $C(CH_3)_3$ | H | $19.3 \pm 4.3$ |
| $OCH_2CH_3$ | $CH_3$ | $23.4 \pm 5.1$ |
| $OCH(CH_3)_2$ | $CH_3$ | $25.8 \pm 5.5$ |
| 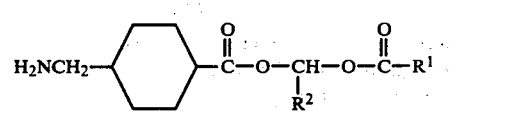 | $CON(CH_3)_2$ | $32.2 \pm 4.7$ |

What we claim is:

1. A compound of the formula $$H_2NCH_2-\bigcirc-\overset{O}{\underset{\|}{C}}-O-\underset{R^2}{\overset{|}{C}H}-O-\overset{O}{\underset{\|}{C}}-R^1 \qquad I$$

and therapeutically acceptable salt thereof, wherein $R^1$ is selected from the group consisting of
(a) alkyl groups containing 1–4 carbon atoms,
(b) alkoxy groups containing 1–4 carbon atoms, (c) ―⟨ ⟩―$CH_2NH_2$ (d) ―⟨ ⟩―$CH_2NH_2$;

$R^2$ is selected from the group consisting of
(a) H,
(b) alkyl groups containing 1–4 carbon atoms,
(c) ―$COOR^3$, wherein $R^3$ is an alkyl group containing 1–4 carbon atoms, (d) —CONR⁴R⁵, wherein R⁴ and R⁵ are the same or different alkyl groups containing 1-3 carbon atoms; or wherein R¹ and R² represent together the radical

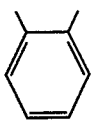

2. A compound according to claim 1 and therapeutically acceptable salts thereof, wherein R² is H or CH₃.

3. A compound according to claim 1 and therapeutically acceptable salts thereof wherein R¹ is an alkyl group containing 1-4 carbon atoms.

4. A compound according to claim 1, and therapeutically acceptable salts thereof, wherein R¹ is an alkoxy group containing 1-4 carbon atoms.

5. A compound according to claim 1, and therapeutically acceptable salts thereof, wherein R¹ is

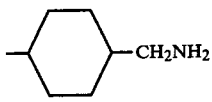

6. A compound according to claim 1, and therapeutically acceptable salt thereof wherein
R¹ is an alkyl group containing 1-4 carbon atoms, an alkoxy group containing 1-4 carbon atoms, or the radical

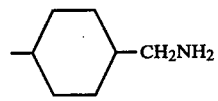

and wherein R² is H or CH₃.

7. A compound according to claim 1, and therapeutically acceptable salts thereof, wherein R¹ is an alkoxy group containing 1-4 carbon atoms and R² is H or CH₃.

8. A compound of claim 1 having the formula

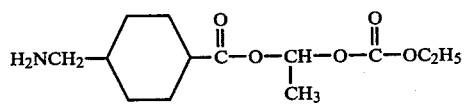

or a therapeutically acceptable salt thereof.

9. A compound of claim 1 having the formula

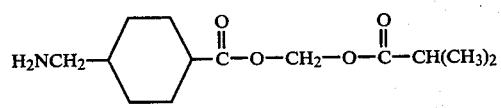

or a therapeutically acceptable salt thereof.

10. A compound of claim 1 having the formula

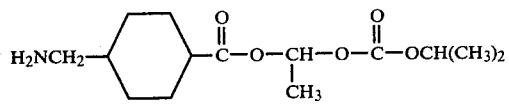

or a therapeutically acceptable salt thereof.

11. A compound of claim 1 having the formula

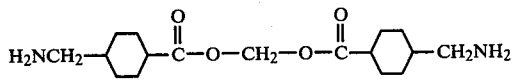

or a therapeutically acceptable salt thereof.

12. A compound according to claim 1 in the form of its trans isomer.

13. A compound according to claim 1 in the form of its hydrochloride.

14. A method for the treatment in mammals and man of ailments due to increased fibrinolysis, characterized by administration to a host in need thereof of a therapeutically effective amount of a compound according to claim 1.

15. A method for the treatment of peptic ulcers in man, characterized in administration to a host in need thereof of a therapeutically effective amount of a compound according to claim 1.

16. A method for the treatment of hereditary angioneurotic edema in man, characterized in administration to a host in need thereof of a therapeutically effective amount of a compound according to claim 1.

17. A pharmaceutical preparation for treatment of ailments due to increase fibrinolysis containing as an active ingredient a compound as defined in claim 1, in an amount effective for treatment of said ailments.

18. The pharmaceutical preparation of claim 16 which is in dosage unit form for oral application containing 50-500 mg. of said active ingredient.

19. The pharmaceutical preparation of claim 17 which is in dosage unit form as a liquid preparation for oral application containing about 0.1% to 20% by weight of said active ingredient.

20. The pharmaceutical preparation of claim 17 which is in dosage unit form.

21. The pharmaceutical preparation of claim 17 which is in dosage unit form for parenteral application by injection containing from 0.1 to 10 mg. of said active ingredient.

22. A pharmaceutical preparation for the treatment of peptic ulcers in man containing as active ingredient a compound as defined in claim 1 in an amount effective for the treatment of peptic ulcers.

23. The pharmaceutical preparation of claim 22 which is in dosage unit form.

24. The pharmaceutical preparation of claim 22 which is in the form of a liquid unit dosage preparation for oral application containing from about 0.1% to 20% by weight of said active ingredient.

25. The pharmaceutical preparation of claim 22 which is in the form of a dosage unit for oral preparation containing 50-500 mg. of said active ingredient.

26. A pharmaceutical preparation for the treatment of hereditary angioneurotic edema in man containing as active ingredient a compound as defined in claim 1 in an amount effective for the treatment of said hereditary antioneurotic edema.

27. The pharmaceutical preparation of claim 26 being in dosage unit form.

* * * * *